United States Patent [19]

Agback

[11] Patent Number: 4,591,584

[45] Date of Patent: May 27, 1986

[54] AZO-BIS-SALICYLIC ACID AND SALT THEREOF, TO TREAT INFLAMMATORY CONDITIONS OF THE INTESTINE

[75] Inventor: Karl H. Agback, Upsala, Sweden

[73] Assignee: Pharmacia AB, Upsala, Sweden

[21] Appl. No.: 709,032

[22] PCT Filed: Jun. 15, 1984

[86] PCT No.: PCT/SE84/00226

§ 371 Date: Jan. 28, 1985

§ 102(e) Date: Jan. 28, 1985

[87] PCT Pub. No.: WO85/00013

PCT Pub. Date: Jan. 3, 1985

[30] Foreign Application Priority Data

Jun. 15, 1983 [SE] Sweden .................. 8303399

[51] Int. Cl.$^4$ ............................... A61K 31/60
[52] U.S. Cl. ................................ 514/160; 534/660
[58] Field of Search .................. 534/660; 514/160

[56] References Cited

U.S. PATENT DOCUMENTS

| | | | |
|---|---|---|---|
| 1,157,169 | 10/1915 | Mettler | 534/660 |
| 1,824,914 | 9/1931 | Microcourt | 534/660 |
| 2,690,438 | 9/1954 | Kracker et al. | 534/660 |
| 4,312,806 | 1/1982 | Lambert et al. | 534/660 |
| 4,455,305 | 6/1984 | Rokos | 514/150 |

FOREIGN PATENT DOCUMENTS

| | | |
|---|---|---|
| A45006 | 7/1981 | European Pat. Off. . |
| 0036637 | 9/1981 | European Pat. Off. . |
| 0036636 | 9/1981 | European Pat. Off. . |

OTHER PUBLICATIONS

Helvetica *Chimica Acta.* 34 (1951), pp. 2076–2083.
Willoughby et al., Gut. 1982, 23, pp. 1081–1087.

*Primary Examiner*—Stanley J. Friedman
*Attorney, Agent, or Firm*—Fred Philpitt

[57] ABSTRACT

The present invention is concerned with compounds having a pharmaceutically acceptable degree of purity, and with formulations of these compounds for the treatment of inflammatory disorders in the intestine (IBD), especially ulcerative colitis. These compounds are 4,5'-azo-bis-salicylic acid (I) and its pharmaceutically acceptable salts, especially the disodium salt. The invention is also concerned with a method for treating inflammatory conditions in the intestine, especially ulcerative colitis. Finally the invention also comprises a method of producing 4,5'-azo-bis-salicylic acid with a pharmaceutically acceptable degree of purity.

4 Claims, No Drawings

AZO-BIS-SALICYLIC ACID AND SALT THEREOF, TO TREAT INFLAMMATORY CONDITIONS OF THE INTESTINE

This invention is concerned with compounds having a pharmaceutically acceptable degree of purity, and with formulations thereof for the treatment of inflammatory disorders in the intestine (IBD), especially ulcerative colitis. The invention comprises also a method of treating inflammatory disorders in the intestine, especially ulcerative colitis. The method comprises oral or rectal administration of a compound according to the invention suitably formulated for its contemplated use; e.g. for oral administration in the form of a tablet or capsule, and for rectal administration in the form of an enema or suppository. The invention finally also comprises a novel method for producing 4,5'-azo-bis-salicylic acid (I) or its salt with a degree of purity that is pharmaceutically acceptable.

Medical treatments of ulcerative colitis have been carried out in various different ways. In particular two methods are now in use to a considerable extent:

Corticosteroids are relied on in severe acute cases, but they have highly objectionable side effects and are therefore unsuitable for more general use. Sulfasalazine is the compound that is being used most generally and most extensively. It is used both in acute phase treatments and prophylactically for preventing an acute condition (relapse prevention effect). Sulfasalazine is believed to exert its effect by being cleared to sulfapyridine and 5-aminosalicylic acid (5-ASA) in the patient's large intestine. The clerage product 5-ASA is believed to be responsible for the therapeutic effect, by direct local action on the intestinal mucosa, while the other clearage product, sulfapyridine, can hardly be considered to have any positive effect against the disease at all but is responsible for most of the side effects of sulfasalazine treatments.

Other methods of treating inflammatory disorders of the intestine comprise local treatment with 5-ASA and oral treatment with 5,5'-azo-bis-salicylic acid (A), carboxyphenylazosalicylic acid (B) and its carboxymethylamide (C). It is believed that when any of these three compounds are administered orally they can be transported to the large intestine where they are then subject to being split in a manner analogous to the splitting of sulfasalazine, to thus form 5-aminosalicylic acid plus another compound: p-aminobenzoic acid or p-aminohippuric acid, respectively. Compounds (A), (B) and (C) may be considered to act as carriers of 5-ASA during transport through the digestive tract. Splitting of the compound 5,5'-azo-bis-salicylic acid gives only 5-ASA.

Moreover it has been found that 4-aminosalicylic acid, PAS, a well-known anti-tuberculosis agent, may be useful in the treatment of ulcerative colitis by rectal administration. Oral administration of PAS or of 5-ASA is not considered to be recommendable because both of these substances are absorbed long before reaching that diseased region of the large intestine which is their desired target region for exerting their local effect.

In the 1950's it was believed that 4,5'-azo-bis-salicylic acid would be a potential tuberculostatic compound in view of the fact that it contains the PAS structure. However, Büchi, J. et al. (Helv. Chim. Acta 34 (1951), p. 2076–83) have shown by in vitro tests that the compound 4,5'-azo-bis-salicylic acid, among others, has a very low tuberculostatic effect—only 1/100 of the effect of PAS. For this reason it seemed out of the question that 4,5'-azo-bis-salicylic acid could be useful as a tuberculostatic agent. Büchi's work also indirectly showed that in his tests 4,5'-azo-bis-salicylic acid was not split to form 5-ASA and PAS: If indeed such splitting had occurred a tuberculostatic effect would have been obtained due to the action of PAS.

It has now surprisingly been found that in contrast to what is inferrable from the work of Büchi the 4,5'-azo-bis-salicylic acid and its salts are split, in the intestine with liberation of PAS and 5-ASA (see Example 6). The discovery of this splitting has been conducive to the elaboration of the present invention, objects of which are (a) providing a composition which is suitable for the treatment of inflammatory disorders of the intestine and which is more efficient and potentially gives less side effects as compared to known analogous compositions containing positional isomers of 4,5'-azo-bis-salicylic acid, (b) providing 4,5'-azo-bis-salicylic acid in a degree of purity that is acceptable for said composition, and (c) providing a novel method of treating inflammatory disorders of the intestine, especially ulcerative colitis.

The invention is thus concerned with a novel composition employed for the treatment of inflammatory disorders of the intestine, especially ulcerative colitis. In addition to a therapeutically active amount of 4,5'-azo-bis-salicylic acid and/or a salt thereof which is pharmaceutically acceptable and therapeutically active, the composition according to the invention may optionally contain a pharmaceutically acceptable carrier and/or a suitable adjuvant. Examples of suitable salts include salts of said acid with pharmaceutically acceptable alkali or alkaline earth metals, and salts with positively charged and pharmaceutically acceptable polymeric carriers.

The compositions according to the invention may take the form of tablets, dragées, capsules, enemas etc. They are produced in a known per se manner in that 4,5'-azo-bis-salicylic acid is mixed with the desired carrier material and/or suitable auxiliary substances to thus give a suitable galenic form. For example, the composition may be coated with a film that is resistant to gastric juice and is dissolved only after it has reached the intestine. When a composition according to the invention is prepared the free acid may be replaced by one or more of its salts which are suitable for the purpose in question. The amount of acid or its salt per dosage unit will vary, depending in each case on inter alia the number of administrations per day, and the individual and total dosages per day.

In accordance with this invention an enhanced effect is obtained due to the use of 4,5'-azo-bis-salicylic acid, or pharmaceutically acceptable salts thereof, instead of for example 5,5'-azo-bis-salicylic acid. The reason for this is that a lesser amount of the two active substances, PAS and 5-ASA, is absorbed from the large intestine as compared to the case where 5,5'-azo-bis-salicylic acid is employed. Due to the decrease of the amount of 5-ASA absorbed into the blood stream and secreted into the urine via the kidneys the risk of a toxic effect being exerted on the kidneys is minimized; and this is the only known toxic effect of 5-ASA. Consequently it is possible to at least double the dose without actually increasing the risk of any such a 5-ASA side effect, as compared with the case where 5,5'-azo-bis-salicylic acid is used.

Table I in Example 6 shows that in the intestine of mice 4,5′-azo-bis-salicylic acid (I) is split to form 5-ASA and PAS, implying that the acid (I) and its salts can be employed for the treatment of inflammatory disorders of the intestine.

Furthermore, it will be seen upon a comparison of Tables I and II that 4,5′- and 5,5-azo-bis-salicylic are equivalent in respect of their low degree of urinary secretion of the intact substance, that 4,5′-azo-bis-salicylic acid leaves about 50% more of the active substances in the colon due to lower absorption and urine secretion, and that 4,5′-azo-bis-salicylic acid is about 5 times better as regards the amount of free 5-ASA secreted via the kidneys.

To sum up, the 4,5′-azo-bis-salicylic acid according to the invention has surprisingly great advantages, in several respects, over 5,5′-azo-bis-salicylic acid. The 4,5′ compound thus may be said to be the potentially superior agent for the treatment of inflammatory disorders of the intestine, especially ulcerative colitis.

4,5′-azo-bis-salicylic acid may be prepared in various different ways. A theoretically conceivable route consists in the diazotization of PAS and coupling of the diazonium salt with salicylic acid in alkaline solution; but instead of the expected product this procedure gives an undefined mixture of polymeric azo compounds. That this theoretically feasible procedure will be thwarted by practical difficulties is made clear by Flury, M. A.: Die Synthese einiger tuberkulostatisch wirksamer Derivate der p-Aminosalicylsäure: Prom Nr 2000, Eidgenöss. Techn. Hochschule in Zürich; Juris-Verlag, Zürich (1951) p. 72-73.

It is also possible to produce 4,5′-azo-bis-salicylic acid in a known manner, e.g. by hydrolysis of 5-(3-chloro-4-carboxyphenylazo)-salicylic acid (II) obtained by diazotizing 2-chloro-4-aminobenzoic acid and azo coupling with salicylic acid. A serious disadvantage inherent in this method is that it is very difficult to obtain the final product (I) free from the chlorine-containing intermediate product (II). For (I) to be useful as a medicine (drug) it must fulfill the special quality requirements applicable to medicines, in particular purity requirements. As a general rule a purity (content) of 98% (w/w) should be the attainable minimum purity guarantee in the case of novel synthesis-based drugs. It is therefore impossible to use the aforesaid method unless the starting material (II) can be removed efficiently. In the present stage of the art, this problem has not yet found a technical-economical solution.

In the present specification and claims, "pharmaceutically acceptable degree of purity" means a purity of 98% or more, with the additional proviso that the product has to fulfill the ordinary quality requirements for medicines.

The starting material for the production of (I) with a pharmaceutically acceptable degree of purity is a compound of formula (III)

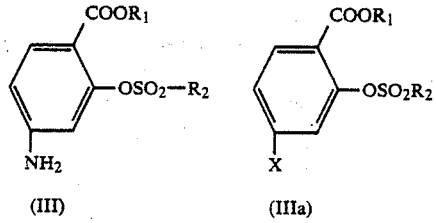

or a salt thereof with an inorganic or strong organic acid. In (III) $R_1$ is a lower alkyl group having up to 5 carbon atoms, preferably methyl, and $R_2$ is a lower alkyl group, preferably methyl, or substituted or unsubstituted phenyl.

Compound (III) may be produced by various different methods which are not comprised by the invention. For example, it may be produced by reduction of the corresponding compound (IIIa) in which $R_1$ and $R_2$ have the same meanings as above and X is a group that is convertible to an amino group, for instance nitro or arylazo, the conversion being effected by means of reduction.

The compound (III) is diazotized in a known per se manner by treatment with nitrous acid in acidic aqueous solution, whereupon the diazonium salt thus formed is coupled in alkaline solution, preferably in the presence of potassium hydroxide, with a compound of formula IV

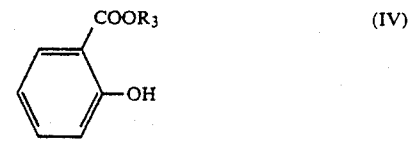

wherein $R_3$ is hydrogen or lower alkyl having up to 5 carbon atoms, preferably methyl.

All of the aforesaid groups $R_1$, $R_2$, $R_3$ must be inert during the coupling step and must be such as to bestow suitable solubility properties on the reactants and products. Also, it is advantageous if these groups are such as to be readily split off from the coupling product.

The product of formula (V)

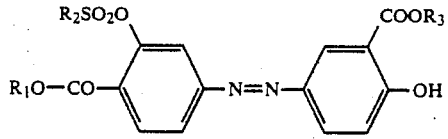

in which $R_1$, $R_2$ and $R_3$ have the same meanings as above is isolated after acidification in a known per se manner and is recrystallized to a desired degree of purity from an organic solvent, e.g. ethyl acetate.

Compound (V) is readily hydrolyzed in water in the presence of an excess of an alkali metal hydroxide. The reaction mixture may also contain a water-miscible solvent. The product (I) is then isolated by acidification with an inorganic acid, for example hydrochloric acid or sulfuric acid. Thereafter if desired compound (I) is reacted in a known per se manner with a suitable salt-forming base to thus form a pharmaceutically acceptable salt. Preferably an alkali metal salt is prepared by partial neutralization of the reaction solution with an acid to a suitable pH for precipitation of the desired salt. More particularly, the disodium and dipotassium salts are obtained in that the reaction solution is acidified to a pH of 5 to 8, preferably 6 to 7, with an inorganic acid or organic acid such as e.g. acetic acid.

The hydrolysis conditions are selected such that the amounts of partially hydrolyzed products are reduced to below a desired level without formation of secondary by-products. For example hydrolysis may be effected by boiling in water for 0.5 to 2 hours and with sodium hydroxide as the alkali metal hydroxide. The resultant product (I) or salt thereof is obtained directly with a degree of purity of 98% or higher, depending on the purity of the intermediate (V). It is very easy to prepare (V) with a desired degree of purity, due to its excellent crystallization properties. Compound (I) on the other hand is comparatively more difficult to purify. For this reason it is imperative that the hydrolysis step be conducted in a manner such that the resultant product (I) directly fulfills pharmaceutical requirements.

The present invention is also concerned with a novel method of treating inflammatory conditions in the intestine, especially in the large intestine, and in particular ulcerative colitis. The method is characterized by rectally or orally administering a therapeutically active dose of 4,5'-azo-bis-salicylic acid or a salt thereof which is pharmaceutically acceptable and therapeutically active. This of course also includes the possibility of administering the free acid together with one or more of such salts.

According to a preferred embodiment, the acid is administered in salt form, and such a salt may advantageously be an alkali or alkaline earth metal salt, e.g. disodium salt of the acid. Administration is usually performed together with a pharmaceutically acceptable carrier and/or a suitable adjuvant.

The daily dose of the active substance, 4,5'-azo-bis-salicylic acid, will vary from case to case and may amount to for instance about 0.1 to about 10 g per day and adult weighing 75 kg. In normal therapy cases, a preferred dose is from about 0.5 to about 5 g per day and 75 kg adult. This preferred dosage will as a rule give a good therapeutic effect while at the same time side effects are kept at an acceptable low level. The total daily dose may be portioned out among a plurality of administrations per day, for instance 1 to 5 administrations. Where the drug is administered in the form of the salt of the acid, the doses mentioned above refer to the corresponding amount of free 4,5'-azo-bis-salicylic acid.

A number of non-limiting working examples are set out below.

EXAMPLE 1

4,5'-azo-bis-salicylic acid (a) Methyl 2-hydroxy-4-nitrobenzoate 2-hydroxy-4-nitrobenzoic acid (25 g) was dissolved in 100 ml of methanol and sulfuric acid (11 ml, density 1.84). The solution was boiled for 24 hrs, whereupon it was poured onto ice water and extracted with chloroform. The chloroform phase was shaken against sodium hydrogen carbonate solution, dried with magnesium sulfate and evaporated. The product was crystallized from methanol. Yield: 21 g.

(b) Methyl 2-methanesulfonyloxy-4-nitrobenzoate

Methyl 2-hydroxy-4-nitrobenzoate (19.7 g) was dissolved in 100 ml of chloroform and triethylamine (15 ml). The solution was kept at a temperature below 15° C., and methanesulfonylchloride (8.6 ml) was added dropwise. The solution was maintained at 50° C. for 1 hr, whereupon it was poured onto ice-hydrochloric acid and extracted with a total of 600 ml chloroform. The solution was dried with magnesium sulfate, treated with active carbon and evaporated. The product was recrystallized from methanol. Yield: 20 g.

(c) Methyl 4-amino-2-methanesulfonyloxybenzoate hydrochloride

Methyl 2-methanesulfonyloxy-4-nitrobenzoate (14 g) and palladium on carbon (0.5 g, 10%) were suspended in 400 ml of acetic acid and hydrochloric acid (5 ml, density 1.18). The suspension was hydrogenated in a Parr hydrogenation apparatus at 250 kPa. The palladium carbon was filtered off, and the solution was evaporated; the crystal mass was washed with ethyl acetate and dried. Yield: 11 g.

(d) Dimethyl 6'-hydroxy-2-methanesulfonyloxy-4,3'-azo-dibenzoate

Methyl 4-amino-2-methanesulfonyloxybenzoate hydrochloride (11 g) was dissolved in 100 ml water and hydrochloric acid (7.5 ml), was cooled with 100 g of ice and was diazotized with sodium nitrite (3.5 g) dissolved in 15 ml of water.

Methyl salicylate (15.2 g) was added to a solution of potassium hydroxide (12 g 85% w/w) in 200 g of ice-water with thorough agitation. The diazonium salt solution was then poured into this salicylate-hydroxide solution, all at once and with vigorous agitation. After 30 seconds the resultant solution was acidified with acetic acid and extracted with chloroform. The chloroform solution was dried with magnesium sulfate, treated with active carbon and evaporated, whereupon the product was leached with petroleum ether and recrystallized twice from ethyl acetate. Yield: 6 g.

(e) Disodium-4,5'-azo-bis-salicylate

Dimethyl 6'-hydroxy-2-methanesulfonyloxy-4,3'-azo-dibenzoate (4.1 g) was added to a solution of sodium hydroxide (2.8 g) in 40 ml water. The solution was boiled for 45 minutes, wherupon acetic acid was added to obtain a pH of about 8. The solution was cooled, slowly; the crystals were filtered off, washed with water and dried. NMR analysis confirmed the identity of the desired bis-salicylate compound. Yield: 3.4 g.

(f) 1 g of disodium-4,5'-azo-bis-salicylate was dissolved in 20 ml of boiling water, whereupon the solution was acidified with acetic acid down to pH 4. After cooling, the product was filtered off, washed with water and dried. Yield: 0.8 g.

EXAMPLE 2

| | |
|---|---|
| 4,5'-azo-bis-salicylic acid (produced according to Ex. 1(f), but with acidification down to pH 2 by means of inorganic acid) | 250 mg |
| starch | 130 mg |
| Mg stearate | 15 mg |
| Aerosil½ 200 (silica particles from Degussa, Federal Republic of Germany) | 5 mg | are mixed homogenously. Water is added, whereupon the mixture is granulated at 60° C. and compressed to form tablets weighing 400 mg.

If desired the tablet may be provided in a known per se manner with a coating of a film which is soluble in the stomach or soluble in the small intestine.

EXAMPLE 3

| | |
|---|---|
| disodium-4,5'-azo-bis-salicylate (acc. to Ex. 1(e)) | 250 mg |
| starch | 135 mg |

-continued

| | |
|---|---|
| Mg stearate | 15 mg | are mixed homogeneously and compressed to form tablets weighing 400 mg.

EXAMPLE 4

100 g of disodium-4,5′-azo-bis-salicylate are dissolved in 10.0 lit. of water. The pH is adjusted to pH 7.5, and the solution is then filled into 100 ml bottles for rectal administration, whereupon the bottles are sterilized.

EXAMPLE 5

250 mg disodium-4,5′-azo-bis-salicylate are filled automatically into gelatin capsules. The bis-salicylate compound is in the form of a crystalline substance having a particle size of 0.1–2.0 mm and produced by sieve screening.

EXAMPLE 6

Pharmacokinetic properties of 4,5′-azo-bis-salicylic acid and 4,4′-azo-bis-salicylic acid Mice were given a single oral dose of 100 mg/kg (in the form of the sodium salt of (I)), whereafter urine was collected for 24 hrs.

The amounts of 4,5′-azo-bis-salicylic acid, Ac-PAS and Ac-5-ASA, and the sum of free PAS+5-ASA, were measured by chemical analysis (Willoughby C. P. et al; Gut 23 (1982) p 1081–87); the method employed (HPLC) did not permit PAS and 5-ASA to be determined separately from each other. "Ac-PAS" and "Ac-5-ASA" mean acetylated PAS and acetylated 5-ASA respectively.

The results are shown in Table I.

TABLE I

| | Amount secreted, % of dose administered | | | |
|---|---|---|---|---|
| | 4,5′-azo-bis-salicylic acid | Ac-PAS | Ac-5-ASA | PAS + 5-ASA |
| Mouse No 1 | 1.4 | 13.4 | 18.7 | 1.7 |
| 2 | 1.3 | 13.8 | 18.3 | 2.3 |
| 3 | 1.0 | 12.5 | 17.5 | 1.7 |
| 4 | 4.6 | 11.7 | 17.7 | 2.7 |
| Average | 2.1 | 12.9 | 18.1 | 2.1* |

*Approximately half of this may be assumed to be 5-ASA

Corresponding tests with 5,5′-azo-bis-salicylic acid (as sodium salt) are shown in Table II:

| | Amount secreted, % of dose administered | | |
|---|---|---|---|
| | 5,5′-azo-bis-salicylic acid | Ac-5-ASA | 5-ASA |
| Mouse No 1 | 1.9 | 59.4 | 2.7 |
| 2 | 1.0 | 46.6 | 5.8 |
| 3 | 1.9 | 47.7 | 5.7 |
| 4 | 2.3 | 57.9 | 7.8 |
| Average | 1.8 | 52.9 | 5.5 |

I claim:

1. A method of treating inflammatory conditions in the intestine, comprising administering to a patient suffering from such condition a therapeutically active amount of 4,5′-azo-bis-salicylic acid or a therapeutically active amount of a pharmaceutically and therapeutically acceptable salt thereof.

2. A method according to claim 1 wherein said salt is an alkali metal salt.

3. A method according to claim 1 wherein said salt is an alkaline earth metal salt.

4. A method according to claim 1 wherein said salt is the disodium salt.

* * * * *